United States Patent
Glatkowski et al.

(10) Patent No.: US 7,195,754 B1
(45) Date of Patent: Mar. 27, 2007

(54) NANOTUBE BASED SUNSCREEN

(75) Inventors: Paul J. Glatkowski, Littleton, MA (US); Joseph W. Piché, Raynham, MA (US); Jeffrey L. Conroy, Rumford, RI (US); Roy Bolduc, Amesbury, MA (US); Pierre LaBlanc, Wakefield, MA (US)

(73) Assignee: Eikos, Inc., Franklin, MA (US)

( * ) Notice: Subject to any disclaimer, the term of this patent is extended or adjusted under 35 U.S.C. 154(b) by 475 days.

(21) Appl. No.: 10/373,181

(22) Filed: Feb. 26, 2003

Related U.S. Application Data (60) Provisional application No. 60/359,362, filed on Feb. 26, 2002.

(51) Int. Cl.
*A61Q 17/00* (2006.01)
*A61Q 17/04* (2006.01)
*A61Q 19/00* (2006.01)
*D01F 9/12* (2006.01)
*A61K 8/00* (2006.01)

(52) U.S. Cl. .......... 424/59; 424/60; 424/400; 424/401; 423/447.1

(58) Field of Classification Search ........... 424/59, 424/60, 400, 401
See application file for complete search history.

(56) References Cited

U.S. PATENT DOCUMENTS

2003/0161803 A1* 8/2003 Vic et al. ............ 424/70.1

* cited by examiner

Primary Examiner—Shelley A. Dodson
(74) Attorney, Agent, or Firm—Novak Druce & Quigg LLP (57) ABSTRACT

This invention relates generally to the incorporation of carbon nanotubes into compositions for protection against damage from ultraviolet radiation. In particular, the invention is directed to sunscreen compositions and methods for the preparation of sunscreen compositions.

29 Claims, 5 Drawing Sheets

Graphite

Diamond $C_{60}$

Single Wall Carbon Nanotube

$$A_D = I_D/I_0 \times 100\%$$

$A_D$ = relative amplification of damaged sample
$I_D$ = intensity of PCR band of damaged sample
$I_0$ = intensity of PCR band of undamaged sample

NANOTUBE BASED SUNSCREEN

REFERENCE TO RELATED APPLICATIONS

This application claims priority to U.S. provisional application number 60/359,362, entitled Nanotube Based Sunscreen, filed Feb. 26, 2002.

BACKGROUND OF THE INVENTION

This invention relates generally to compositions containing carbon nanotubes for protection from exposure to harmful ultraviolet radiation and, in particular, to sunscreen compositions containing carbon nanotubes.

1. Field of the Invention
2. Description of the Background

Although exposure to the sun's UV rays is said to be the most important factor in the cause of skin cancers, about 70 percent of American adults do not use sun-protection measures. Currently available formulations provide significant protection from the UVB portions of the spectrum; however, few commercial products offer complete UVA/UVB protection. While UVB radiation accounts for most of the sunburn damages, UVA is responsible for deeper damage to melanocytes and the ensuing melanoma. Incomplete UV blockage precludes full protection from DNA damage and immunosuppression, both of which are induced by UV radiation. In addition, most formulations that block UVA contain irritants that lead to allergic reactions or may develop into toxic agents upon exposure to UV radiations.

Preliminary work in our laboratories has confirmed that multiwall carbon nanotubes (MWNT) effectively block UV transmission in the range from 290 to 400 nm. In the field of material science, carbon nanotubes offer physical properties (such as thermal and electrical conductivity, and tensile strength) that make it suitable in a multitude of applications. We propose to take advantage of the light absorbing properties of carbon nanotubes to develop a sunscreen/sunblock formulation offering (1) complete shielding from UVAs and UVBs and (2) order of magnitude improvement over current products for protection from associated DNA damage and immunosuppression. In addition, potential toxicities associated with the topical application of carbon nanotubes will be identified and eliminated to develop not only a sunscreen with no adverse allergic reactions but also an efficient method of nanotube incorporation into safe, effective commercial products.

The plan will lead to the development of a sunblock formulation that can be used commercially with order of magnitude improvement in UVA and UVB protection over current off the shelf products, with protection from UV-induced immunosuppression, and with no adverse allergic or photoallergic reactions. Phase I will focus on development of a novel nanotube filter in a sunscreen/sunblock vehicle capable of full UVA/UVB blocking. The carbon nanotube suspensions will allow us to initiate further studies into the toxicities of single walled carbon nanotubes (SWNT) in order to eliminate this pitfall and provide a safe, effective method for SWNT incorporation into commercial products. Phase II will consist of clinical studies to determine the efficacy of the formulation to protect against the damaging effects of UV radiation including the immunomodulation properties of SWNT present in a sunscreen. Validation of the sunblock formulation will prove its efficacy for use in various cosmetic products for which sunblocking properties represent an added marketing advantage.

Figure 1:
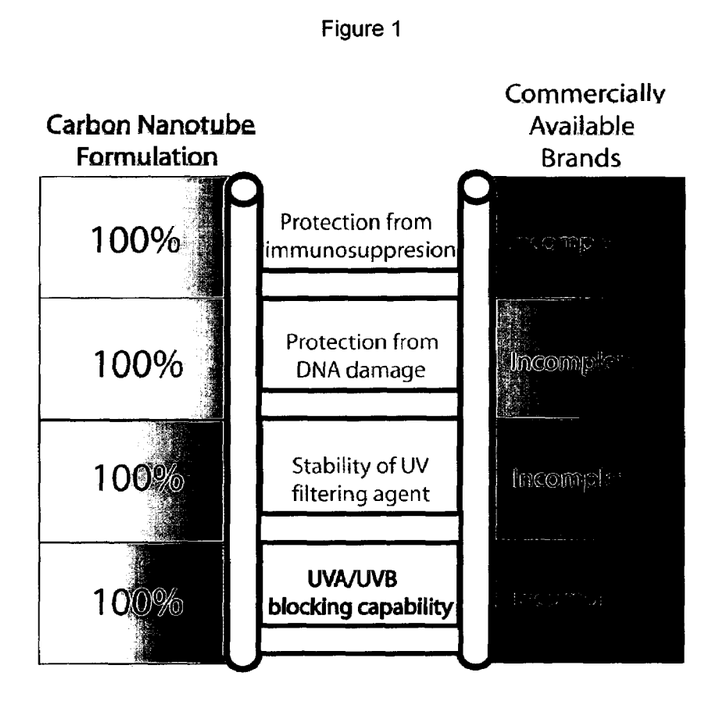
FIG. 1. Laddered comparison of commercially available sunscreens and the carbon nanotube formulation. Only the sunscreen incorporates a fully stable UV filter offering complete protection from UVA/UVB radiation and its associated health hazards.
Figure 2:
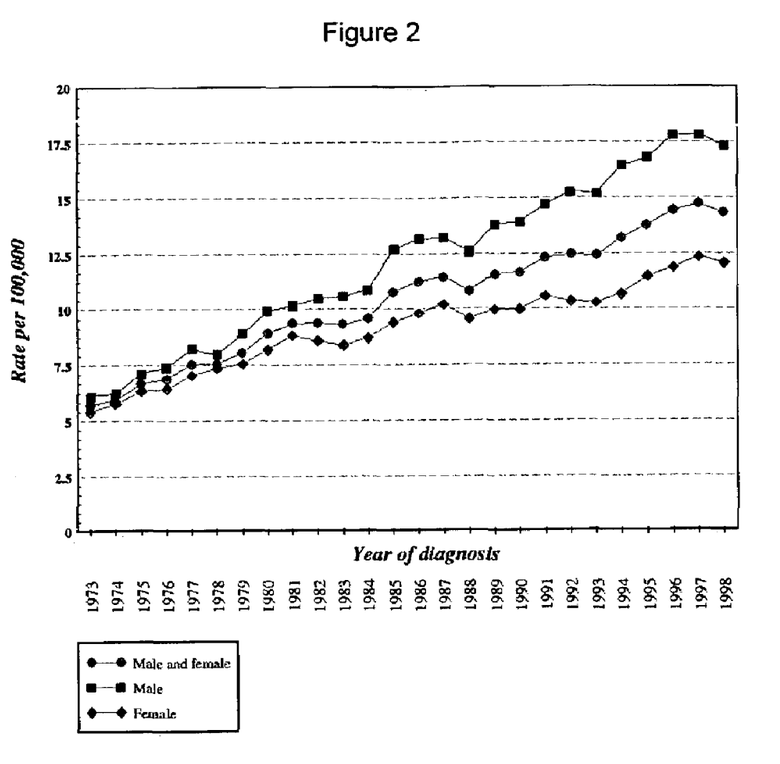
FIG. 2. Yearly incidence of skin cancer according to sex. Rates are expressed as cases per 100,000. Source: Surveillance, Epidemiology, and End Results (SEER) Program of the National Cancer Institute.

Cancer of the skin is the most common of all cancers in the United States, comprising over half of all cancer diagnoses. As seen in FIG. 1, the incidence of skin cancer in the U.S. has been rising at an epidemic rate, more than doubling itself in the female population and nearly tripling itself in the male population since 1973. In 2001, one million new cases of non-melanoma skin cancer and 51,400 new cases of melanoma skin cancer were reported in the U.S. While melanoma skin cancer represented only 5 percent of all skin cancers in the U.S. in 2001, it accounted for 80% of all skin cancer deaths (equating to approximately 7,800 deaths per year).

There are three main types of skin cancer: (1) melanoma, (2) basal-cell carcinoma, and (3) squamous-cell carcinoma, the latter two being also known as non-melanoma skin cancers. Basal cell carcinoma is normally not lethal but may spread to the bone. Squamous-cell carcinoma can be lethal if not detected early and treated. The deadliest of the skin cancers is by far melanoma. Melanomas spread quickly from skin cells to other organs, most notably the liver, lungs, bones, and brain.[1] Ultraviology B (UVB) radiation (280 to 320 nm) has been implicated in the development of non-melanoma and melanoma skin cancers. Ultraviolet A (UVA) radiation (320 to 400 nm) has been shown to exacerbate the detrimental effects of UVB and according to recent studies, may also have a direct effect on melanoma development.[2] UVC radiation (100 to 280 nm) does not pose a threat as its ray cannot penetrate earth's atmosphere. Clearly, sunscreen formulations must be capable of blocking both UVA and UVB to achieve maximum effectiveness and eliminate the risk of skin cancer development.

The penetration of UV thorough the skin varies from 0.1–1.0 mm depending on the intensity and wavelength. Excessive exposure to UVB, which exhibits shorter wavelengths than UVA, usually results in topical sunburn.[3] This is clinically known as erythema and first appears as reddening, initially at about 2–6 hours after exposure and increasing in intensity to about 24 hours. Longer wavelength UVA rays penetrate deeper into the skin than UVB, weakening inner skin tissue and accelerating skin aging.[4] Artificial UVA radiation, used for cosmetic tanning, is as dangerous as its natural counterpart and is thought to be capable of inducing nonmelanoma skin cancer.[5,6] Premalignant keratoses, but not cancers, have been observed in users of tanning beds.[7] UV overexposure has also been shown to damage skin membranes and DNA as well as suppress the immune system.[8,9,10] It is believed that the immune systems "T" cells can be suppressed from fighting melanoma target cells for up to 3 weeks following overexposure and sunburn. The long-term consequences of overexposure include skin cancer, photosensitivity and premature skin aging.

Controversy exists in the scientific and medical communities as to the most dangerous type of UV exposure. Although UVB rays are responsible for producing melanin and for thickening the skin's outer layer as protection against sun damage, it has been argued that UVB is more harmful than UVA because it damages cell DNA through formation of cyclobutane pyrimidine dimmers and 6-4 photoproducts. UVA radiation more weakly induces these forms of DNA damage through an oxidative pathway. UVA rays also penetrate more deeply than UVB rays, thus damaging the dermis, the innerlayer of skin that contains the blood vessels, hair follicles, and nerve endings, and ultimately accelerating skin aging. As detrimental effects are associated with each type, a filter capable of blocking both UVA and UVB is necessary for an effective sunscreen formulation.

It is generally agreed that UV radiation not only suppresses the immune response of cells in the skin, contributing to the development of skin cancers, but may also induce generalized immune suppression and have an important impact on how people tight off infectious diseases. In the mouse model of sun exposure, induction of antigen-specific suppression appears to be linked to Fas ligand (FasL). It was shown that normal mice acutely exposed to UV exhibited a profound suppression of both contact hypersensitivity and delayed type hypersensitivity (DTH) reactions and the development of transferable antigen-specific suppressor cells. These reactions were found to be lacking in FasL-deficient mice. Therefore, Fas/FasL interactions are essential for systemic UV-induced suppression of immune responses that involve host antigen presentation and suggest an interrelationship between UV-induced DNA damage and FasL in this phenomenon. The emerging picture is that UV-induced DNA damage disarms the immune system in a manner similar to that observed in immunologically privileged sites. Further studies by Hill and his colleagues demonstrated that FasL is responsible for the accumulation of p53 mutations in UV irradiated mice[11]. Therefore, there is an important need for broad spectrum sunscreen/sunblock formulations that are capable of significantly reducing the damages from UVA and UVB and prevent immunosuppression.

SUMMARY OF THE INVENTION

The present invention overcomes the problems and disadvantages associated with current strategies and designs, and provides compositions containing carbon nantotubes for the protection against harmful effects associates with ultraviolet and other types of radiation.

Accordingly, one embodiment of the invention is directed to compositions that contain carbon nanotubes.

Other embodiment and technical advantages of the invention are set forth below and may be apparent from the drawings and the description of the invention which follows, or may be learned from the practice of the invention.

DESCRIPTION OF THE INVENTION AND EXAMPLES

As embodied and broadly described here, the present invention is directed to compositions containing carbon nanotubes for the protection against ultraviolet and other harmful radiation.

There is a rather long list of chemical agents that are and have been used to effectively block UV rays. Current sunblock formulations consists of chemical or physical filters. Studies on effectiveness of UVA/UVB blocking abilities show a slight advantage for the chemical formulations over the physical formulations. This is explained in part by the ease of application of the chemical formulations (i.e. use more of the chemical vs. the physical formulations e.g. thicker coating). Interestingly, both types of formulations are tested for their ability to protect against erythema, but not for their potential to spare the immune system. Para-aminobenzoic acid (PABA) was a popular chemical filter used widely until it was found to be a fairly common sensitizer. Furthermore, its tendency to cross-sensitize with compounds of similar chemical structure that are used topically or systemically has lead to its removal from sunscreen preparations. It is important to note that it has been reported that continued exposure to chemicals of this type could lead to autoimmune responses, especially systemic lupus erythematosus and dermatomyositis.

Laboratory testing of current formulations of sunscreen (chemical or physical) have shown that, in general, they all reduce erythema formation effectively. However, a recent analysis of the chemical agents upon prolonged exposure to UV rays revealed that these agents are not stable. The stability tests were performed by applying a thin film of the sunscreen preparation to the wall of a quartz window, irradiating it with a sun simulator, and measuring the absorbance with spectrophotometry before and during irradiation. The sunscreen agent studied most thoroughly was the UVB filter octyl methoxy cinnamate, but other UVA and UVB filters and some commercial products were also tested. Considerable breakdown of most filters was observed after doses of irradiation equivalent to moderate sun exposure. It can be questioned whether the breakdown products of sunscreens also possess other physical or biological properties. Few studies looking at the immunological consequences of UV exposures in the presence of these UVA and UVB filters have found complete protection from the immunosuppression that has been reported in the past. In addition, the allergic and sensitivity reactions ensuing from topical application of these products are not surprising since all topical agents penetrate the skin to an extent. Some chemical filters penetrate deeper than others and therefore the potential to develop sensitization and allergy to these components is greater.

Chemical agents are not the only ones that suffer during UV irradiation. Metal oxides have the disadvantage of free radical generation upon UV exposure and may react topically with the sunscreen vehicle to yield local damage and/or contribute to adverse reactions (such as immunosuppression). Van der Molen and colleagues showed that a $TiO_2$ preparation when applied without subsequent UVB irradiation also induced a significant decrease of the mixed epidermal cell lymphocyte reaction (MECLR) responses. Moreover, the same compound affected the intercellular lipid layers, and desmosomes could not be detected. The deleterious effect of this compound is probably caused by an incomplete hydrolysis during the $TiO_2$ synthesis. It has been found that micronized pigment-containing compounds can offer good protection against short-term UVB-induced immunomodulation in humans in vivo. However, accurate screening of the synthesis of these compounds is a prerequisite for their safe use as sunscreening agents. The effectiveness of these agents on UVA protection at the erythema and immune suppression levels are incomplete.

The results gathered to date support the view that a broad base UVA/UVB blocking agent that is biologically inert, stable to UV radiation, and easy to produce would be welcomed by the medical, scientific, and cosmetic communities.

Carbon nanotubes are fullerene-related structures consisting of graphene cylinders closed at either end by caps containing pentagonal rings. They were discovered in 1991 by the Japanese electron microscopist Sumio Iijima while studying the material deposited on the cathode during that arc-evaporation synthesis of fullerenes. He found that the central core of the cathodic deposit contained a variety of closed graphitic structures including nanoparticles and nanotubes, of a type which had never previously been observed. A short time later, Thomas Ebbesen and Pulickel Ajayan, from Iijima's lab, showed how nanotubes could be produced in bulk quantities by varying the arc-evaporation conditions. This paved the way to an explosion of research into the physical and chemical properties of carbon nanotubes in laboratories all over the world.

A major event in the development of carbon nanotubes was the synthesis in 1993 of single-layer nanotubes. The standard arc-evaporation method produces only multilayered tubes. It was found that addition of metals such as cobalt to the graphite electrodes resulted in extremely fine tubes with single-layer walls. The availability of these structures should enable experimentalists to test some of the theoretical predictions which have been made about nanotube properties.

An alternative method of preparing single-walled nanotubes was described by Smalley's group in 1996. Like the original method of preparing C60, this involved the laser-vaporization of graphite, and resulted in a high yield of single-walled tubes with unusually uniform diameters. These highly uniform tubes had a greater tendency to form aligned bundles than those prepared using arc-evaporation, and led Smalley to christen the bundles nanotubes "ropes".

Figure 3:
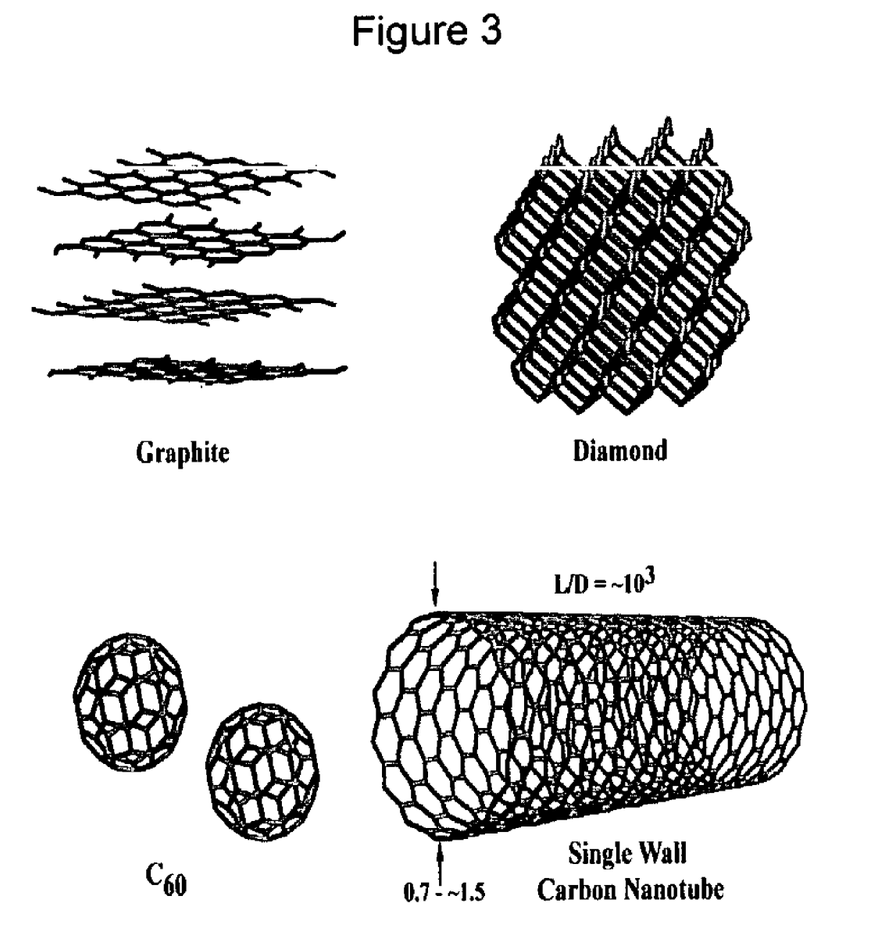
FIG. 3. Structures of various carbon entities. Single wall carbon nanotubes consist of nanometer scale diameter stretched Buckytube rolled graphitic carbon in a single layer.

Carbon nanotubes are now readily synthesized in gram quantities in laboratories all over the world, and are also being offered commercially. Carbon nanotubes are essentially single graphite layers wrapped into tubes, either single walled (SWnT), as shown in FIG. 3, or multi walled (MWnT) wrapped in several concentric layers. SWnTs are composed of a single wall of a hexagonally-bonded graphene sheet (graphite is made of graphene sheets stacked like pancakes). Like the archetypal fullerene, C60, they divide space into two volumes, an inside and an outside, separated by a chemically robust, one-atom thick, impermeable membrane. The perfection of the bonding of this graphene membrane gives such fullerene carbon nanotubes outstanding properties, including:

- electrical conduction equivalent to metals like copper and gold
- thermal conductivity along the tube axis equal to or better than that of any other material
- tensile strength expected to be higher than any other material
- 30–100 times higher strength than steel at one-sixth the weight
- extreme stiffness combined with ability to withstand repeated bending, buckling, twisting, and/or compression at high rates with complete elasticity.
- effective blocking of UV radiation from 290 to 400 nm The unique energy absorption characteristics of carbon nanotubes can provide a highly stable UVA and UVB broadband absorber for sunscreen applications. The main mode of UVA blockage using nanotubes is absorption and not the scattering methods used by zinc oxide, titanium dioxide and a range of other materials. The nanotubes act as a damped, harmonic oscillator, and nanotube length needs to be one half of the wavelength of light. In this case, the wavelengths are 320 nm to 400 nm (UVA) so the nanotubes needed are from 160 nm to 200 nm long. This is easily performed by two central methods; ultrasonics, and acid treatments and we have the ability to disperse and cleave nanotubes. We currently have projects in house that utilize carbon nanotubes for stealth coating applications in which the carbon nanotubes are utilized in a similar approach.

Graphite is the closest carbon substance to carbon nanotubes that has been used in clinical studies. The development of new carbons based on graphite to considerably improve its physical properties has enabled the manufacture of endoprostheses made from carbon. Few reports exist about the toxicity of graphite. Graphite plugs inserted in the femur of rabbits had virtually no effect on bone growth and structure. It is noteworthy that others have reported some form of immune reaction to polymers containing graphite. At low concentration (1–100 mg/m3 synthetic graphite), graphite dust showed poor stimulation of alveolar macrophages.

The effective UVA/UVB blocking properties of nanotubes elevates these carbon structures to ideal sunscreen/sunblock candidates. Indeed, no commercially available product can claim to completely block UVA/UVB rays as nanotubes have been shown to do in our laboratories. Phase II research will be centered on clinical testing of the nanotube suspension formulated in Phase I to prove complete UVA/UVB filtering as well as minimized immunosuppression associated with UV exposure, a protection not afforded with current products. The fact that related graphite structures have not been reported to cause extreme cases of toxicity in subjects suggests that nanotube suspensions can be formulated into a safe product for topical application. This effort will ultimately provide a sunblock filter exhibiting order of magnitude improvement in complete combined UVA/UVB shielding and immunosuppression protection over currently available formulations. The research conducted will also be invaluable to the nanotube community by providing a method of nanotube incorporation into a commercial product for safe use without toxic side effects.

The introduction of a nanotube sunscreening filter, with an associated "SPF infinity", will, no doubt, impact the sun protection market in a manner not seen since the discovery of the damaging effects of UV itself. Current marketed sunscreen lotions and cosmetics, while offering partial blockage of UV radiation, lay no commercial claim on complete protection from DNA damage and immunosuppression, as these issues are not widely known by the public and thus have no current market value. Yet if the public were to be informed of these hazards through the introduction of a new commercial product addressing these recently discovered concerns, consumer spending for sunscreen products would likely become skewed toward the formulation offering complete UV protection.

The principle goal of this proposal is to develop a novel sunscreen filter with full UVA/UVB blocking capabilities and protection from UV-induced immunosuppression and without overt biological activity. This effort will lead to the development of a safe, effective method for incorporation of the filter into a sunscreen/sunblock lotion, a method that may ultimately be used by the cosmetics industry for addition of UV protection to products. Our approach will begin with the preparation of suspensions of SWNT in various vehicles and demonstration of their ability to block UVA/UVB transmission. To accomplish this goal, the following tasks have been identified:

I. Development of carbon nanotube suspensions for inclusion in a sunscreen/sunblock
II. Testing of the carbon nanotube suspensions for their ability to block UVA/UVB
III. Testing of the carbon nanotube suspensions for intrinsic toxicity
IV. Testing of the carbon nanotube suspensions for protection from immunosuppression and DNA damage SWNT and MWNT are obtained from vendors such as Rice University (Houston, Tex.) or DEAL. Purified carbon nanotubes are typically sold as suspensions in organic solvents (methylene chloride). In order to produce water soluble suspensions, the solvent is evaporated and/or exchanged with a water-based solvent. The size of the nanotubes is then reduced by sonication at 50% of maximum with short bursts on ice. A range of carbon nanotubes concentrations will be tested. We will start with a 2% as the most concentrated suspension and then produce more dilute suspensions in the same solvent. After various nanotube suspensions are developed, they will be incorporated into commercially available tanning lotion and UVB SPF2 sunscreen vehicles.

Figure 4:
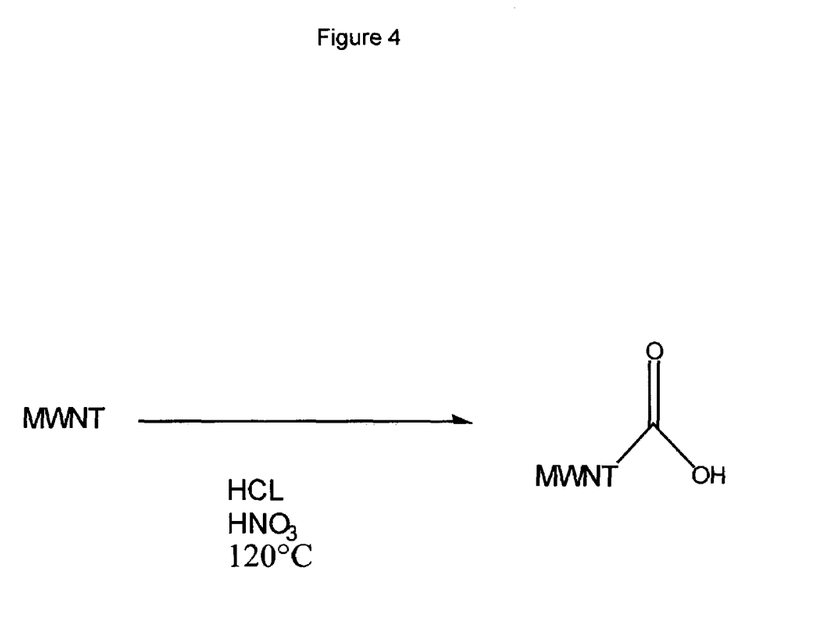
FIG. 4. Reaction for production of derivatized nanotubes.
Figure 5:
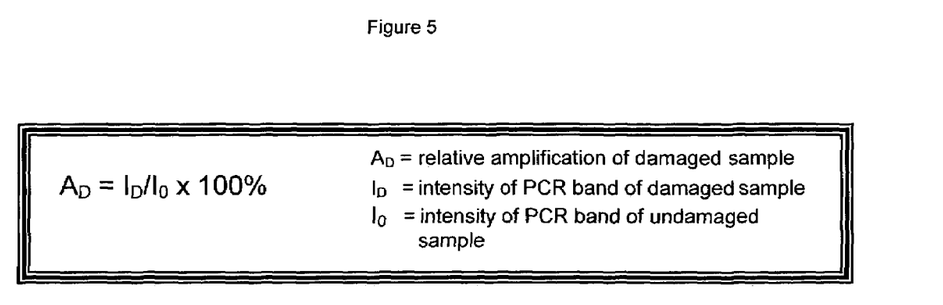
FIG. 5. Equation for the calculation of relative PCR amplifications (established by Kalinowski et al.).

To have greater flexibility of solutions as well as sunblocking and biological properties, we will also test derivatized nanotubes. This reaction, as seen in FIG. 4, produces disentangled and functionalized MWNT and begins with 40 ml 98% Sulfuric Acid ACS grade (Sigma-Aldrich, St. Louis, Mo.), 2.0 grams Carbon Nano Tubes (DEAL International Inc.), and 13.3 ml 60% Nitric Acid ACS grade (Sigma-Aldrich).

A 100 ml 3 neck round bottom flask equipped with a stir bar, condenser, $N_2$ inlet, and ground glass stoppers (with Teflon sleeves) is charged with 40 ml of 98% sulfuric acid, 2.0 grams of carbon nano tubes, and 13.3 ml of 60% nitric acid. The above mixture is then stirred at room temperature for about an hour. After stirring for an hour at room temperature the stirring is continued and the reaction mixture temperature is raised to 120° C. The reaction mixture is maintained at this temperature for 15 minutes after which the heat source is removed. After the slurry is cooled to room temperature, the treated nanotubes are recovered using a centrifuge. The product is washed five times with 40 ml portions of deionized water. A 0.050 mg portion of the treated product is dispersed in ethanol using an ultrasonic wave dispersion technique.

The advantage of this approach is the variety of homogenous solutions that result from the procedure for addition to suitable sunscreen vehicles. Also, water based solutions ease toxicity testing during the addition of the substances to tissue culture medium.

However, carbon nanotubes may fail to stay in solution. Preliminary data indicate that acid treated and sonicated carbon nanotubes remain in suspension for an extended period of time. In the event that settling becomes noticeable, we will add small percentages of detergents and polyols commonly found in consumer products such as glycerol, PEG-60, benzyl alcohol etc. to the nanotube suspensions. Another approach consists of using functionalized SWNT as these are readily soluble in polar solvents.

After inclusion of carbon nanotube suspensions into commercially available tanning lotion and UVB SPF2 sunscreen vehicles, we will test the UVA/UVB blocking properties of all formulations. Our approach will consist of coating quartz discs with various thicknesses of the formulations and measuring their ability to prevent UV light transmission at wavelengths ranging from 290 to 400 nm. Formulations of varying percentages of carbon nanotubes will be used to coat the quartz discs. The light absorption properties of carbon nanotubes strongly suggest that we should see a significant drop in UVA/UVB transmission. Each sample will be corrected for contributions from the vehicle.

Based on preliminary data in organic solution, reduction in nanotube properties is not anticipated. However, experimentation with varying thickness and nanotube percentage will address and help to eliminate any reductions that may arise.

To develop a sunscreen capable of protecting from all deleterious UV effects, the nanotube formulations, after UVA/UVB blocking ability has been established, must be tested for protection from immunosuppression and DNA damage. However, as this testing will be extensive, we find it advantageous to first test for toxicity, so as not to invalidate any optimizations made during the protection studies. Current formulations of carbon nanotubes have yet to be tested for toxicity. Prior to testing on humans, we will test the developed formulations for effects on a number of marker genes. It is important to note that purified carbon nanotubes are supplied as suspensions in organic solvents that may themselves be toxic. To address this issue, organic solvents will be evaporated and/or exchanged with water-based solvents, as described in Task I above.

Toxicity testing will be performed using Xenometrix stress gene assays (Boulder, Colo.). The assays use bacteria, liver and colon cells as hosts for the induction of specific genes after exposure to a test compound, i.e. nanotube formulations. By using the *E. coli* cells as well as mammalian cells to host a battery of 13 reporter constructs, this Gene Profile Assay enables the user to assess fundamental processes of toxicity that are relevant to both bacteria and mammalian cells. The construct battery covers the assessment of biological activities and toxicity associated with: DNA damage, oxidative stress, protein perturbation, and metal contamination. The goal of this assay is to detect a variety of transcriptional responses in *E. coli*. The bacterial promoters included in this assay are fused to the lacZ structural gene. The thirteen lacZ-fusion constructs included in the kit are: hydrogen peroxidase I (katG), mRNA-interfering complementary RNA (micF), high osmolarity induced gene (osm Y), universal stress gene (uspA), a LexA repressed gene (recA), glucose-6-phosphate (zwf), heat shock protein (clpB), DNA damage gene (umuDC), mercury reductase (merR), DNA repair methyltransferase (ada), DNA damage by oxidative stress (dinD), superoxide inducible gene (soi28), endonuclease IV (nfo).

Possible ingestion of SWNT may lead to unexpected metabolic reactions and therefore the Xenometrix test with human liver HepG2 cells will give us an indication of their toxicity on the liver. Using the human liver cell line HepG2, and a battery of 13 reporter constructs, this assay generates Gene Profiles for fundamental pathways of biological activity and toxicity. Cellular events such as DNA damage, protein perturbation, cell cycle perturbation, oxidative stress, metal ion contamination, aromatic hydrocarbon metabolism, signal transduction and retinoid activity can all be assessed. The aim of this assay is to detect a variety of transcriptional responses in human liver cells. The assay utilizes chloramphenicol acetyl transferase (CAT) reporter constructs driven by wild-type promoters or response elements from genes known to play a pivotal role in the liver's response to foreign substances. Thirteen stably transfected cell lines are supplied in along with the parental HepG2 liver cell line for a concurrent cellular viability assessment. The CAT-fusion constructs included in the kit are: cytochrome P450 1A1 (CYP1A1), xenobiotic response element (XRE), glutathione S transferase Ya subunit (GSTYa), human metallothionein-IIA (HMTIIA), retinoic acid response element (RARE), c-fos (FOS), collagenase (XHF), NFkB response element (NFkBRE), cyclic AMP response element (CRE), growth arrest and DNA damage responsive genes (GADD153 and GADD45), p53 response element (P53RE), heat shock protein 70 (HSP70), glucose regulated protein 78 (GRP78).

In addition, test on the colon cells would provide further information on the toxicity of SWNT upon ingestion. The goal of this assay is to detect transcriptional responses related to DNA damage in human colon cells. The assay utilizes chloramphenicol acetyl transferase (CAT) reporter constructs driven by wild-type promoters or response elements from genes known to play a pivotal role in the cell's response to DNA damage. Seven stably transfected cell lines are supplied in each kit along with the parental RKO cell line for a cellular viability assessment. The CAT-fusion constructs included in the test are: DNA polymerase β promoter (βPOL), p53 response element (P53RE), growth arrest and DNA damage responsive genes (GADD45 and GADD153), c-fos (FOS), TPA response element (TRE), and tissue plasminogen activator (tPA).

Although this battery of tests is quite extensive, Xenometrix indicated to us that they are in the process of developing keratinocyte based assays. Although they assured us of the appropriateness of their current assay system to establish the toxicity of our carbon nanotubes suspensions we will test their keratinocytes based assays when they become available.

Broad spectrum UVA/UVB sunscreens do not completely block UV transmission to the skin and thus do not offer complete protection against DNA damage and immunosuppression upon sun exposure. In fact, the public has been kept in the dark about these medical issues, allowing commercialization of current products that are incapable of addressing these problems. In order to create a novel nanotube sunscreen for complete protection from UV and its detrimental effects, nanotube formulations will be extensively tested and optimized for protection from UV-induced immunosuppression and DNA damage. Fas ligand (FasL) and other apoptotic end products will be used as markers to monitor UV-induced immunosuppression occurring with and without sunscreen protection. A PCR-based method designed by Gareth Jenkins and James Parry of the University of Wales, Swansea, will be employed to monitor UV-induced DNA damage with and without the nanotube sunscreen formulations.

UV exposure induces immunosuppression in cells, the mechanism of which can also lead to a cascade of molecular events ending in cell death. Interactions between Fas and Fas ligand (FasL) are essential for systemic UV-induced suppression of immune responses. Engagement of Fas by FasL on target cells, particularly keratinocytes, also triggers a cascade of subcellular events that ends in apoptosis. Prior to apoptosis, nuclear matrix proteins (NMPs) make up the internal structural framework of the nucleus, are associated with such functions as DNA replication, RNA synthesis, and hormone receptor binding, and have been shown to be highly insoluble in vitro However, it is now known that cell death releases soluble nuclear matrix proteins that can be detected in culture supernatants as evidence of dead and dying cells.

Nanotube formulation protection from immunosuppression will be tested using an assay based on the work by Hill and co-workers. The principle of the assay consists of measuring Fas-ligand (FasL) in keratinocytes exposed to UV radiation in the presence or absence of nanotube formulations. In addition we will measure the level of apoptosis induced by UV exposure. The human keratinocyte cell line NCTC 2544 will be cultured in petri dishes in RPMI 1640 in the presence of fetal bovine serum (5%), non-essential amino acids, sodium pyruvate and beta-mercaptoethanol. Prior to exposure to UV radiation, the medium will be removed and cells rinsed with sterile PBS. The lid of the petri dishes will be replaced with a sterile quartz disc that will be coated with different sunscreen preparations. The exposure time will vary from 15 to 60 minutes. Post-UV exposure, cells will be returned to their regular growth medium and aliquots of the supernatants will be collected at various time points in order to measure the level of nuclear matrix proteins (NMP), a marker of apoptosis, and the level of soluble FasL. At the same time intervals, cells will be collected and after lysis, the lysate will be used to measure the level of FasL by ELISA.

An assay for nuclear matrix protein (NMP) 41/7 measurement will also be employed as a secondary measurement of apoptotis in UV-irradiated cell populations either protected with nanotube formulations or left fully exposed. The Cell Death Detection (Nuclear Matrix Protein) ELISA manufactured by Oncogene Research Products (San Diego, Calif.) and available through Calbiochem (San Diego, Calif.) is a sandwich enzyme immunoassay utilizing mouse monoclonal antibodies for quantitation of soluble NMP 41/7. A mouse monoclonal antibody, specific for NMP 41/7, is immobilized onto the surface of the provided plastic wells. The assay sample (irradiated cell supernatants) is pipetted into the wells and a 1.5 hour incubation follows, during which any NMP 41/7 contained in the samples or standards is captured. After unbound material is washed away, a digoxigenin labeled detector monoclonal antibody is added to specifically recognize and bind any NMP 41/7 captured during the first incubation. After a second incubation and wash step, an HRP-linked sheep anti-digoxigenin antibody is used for detection of NMP 41/7 antibody sandwiches. Unreacted components are again removed by washing. A chromogen solution is then added to all wells to produce a colored product in wells containing antibody sandwiches. The production of the colored end product is proportional to the amount of soluble NMP 41/7 present in the original sample. Therefore, quantitative results are obtained by absorbance readings at 450–595 nm. A standard curve can be constructed from the data, and sample values are then easily determined. This assay is very flexible and permits freezing of the samples prior to analysis. For the proposed effort, we expect a huge increase in NMP released upon exposure to UV without protection with sunscreen.

Engagement of Fas by FasL on target cells has been implicated in UV-induced suppression of immune responses and has been seen to trigger a cascade of subcellular events that ends in apoptosis. To test the efficiency of nanotube formulations, soluble and membrane-bound FasL production will be directly monitored in post-UV-irradiated cell supernatants and extracts with and without nanotube formulation protection. To this end, the Fas Ligand ELISA, manufactured by Oncogene Research Products (San Diego, Calif.) and distributed by Calbiochem (San Diego, Calif.), will be used. This ELISA is a "sandwich" enzyme immunoassay employing mouse monoclonal antibodies. A monoclonal antibody, specific for the human FasL protein, has been immobilized onto the surface of microtiter wells by the manufacturer. The assay sample and the biotinylated detector monoclonal antibody are pipetted into the wells prior to a three hour incubation, during which time any FasL in the sample is captured by both antibodies. After unbound material is washed away, horseradish peroxidase-conjugated streptavidin is added to bind the detector antibody. Horseradish peroxidase catalyzes the conversion of the colorless substrate tetra-methylbenzidine (TMB) to a blue reaction product (or yellow after the addition of stop reagent). The intensity of the colored solution is proportional to the amount of FasL protein in the sample, which can be quantitated by spectrophotometry and the construction of a standard curve using known FasL concentrations.

In the assays described above, we expect a dramatic decrease in FasL production and NMP 41/7 detection in cell populations protected with the nanotube formulations when compared to the same populations left fully exposed to UV radiation.

Once non-toxicity is established by the Xenometrix stress gene assays (see Task II above), which test the nanotube formulations for, among other things, intrinsic DNA damaging properties, ability of the formulations to protect from UV-induced DNA damage must be studied and optimized. UVB damages cell DNA through formation of cyclobutane pyrimidine dimmers and 6-4 photoproducts while UVA radiation more weakly induces these forms of DNA damage through an oxidative pathway. A PCR-based methodology designed by Jenkins and Parry will be employed to test for the presence of damage in post-UV-irradiated DNA, both with and without nanotube sunscreen protection. The method relies on the fact that lesions within DNA stretches preclude new synthesis by inhibiting polymerases. Therefore, damaged DNA is a poor template for amplification, and UV-induced DNA damage can be easily detected by a reduction in the amount of amplified PCR product.

The method is divided into several distinct steps: (1) target DNA preparation, (2) target DNA immobilization, (3) UV irradiation of the target DNA in the presence or absence of sunscreen, (4) nested amplification attempt for UV-irradiated DNA template, and (5) detection of the extent of amplification. The method has been modified below to suit our facility and purposes.

Target DNA preparation is achieved by PCR amplification of an approximately 1.7 kilobase region. As we have performed extensive cloning of the *Plasmodium falciparum* malarial parasite, a 1.7 kilobase target can be easily amplified with one in-house primer and one biotinylated primer purchased commercially.

Target DNA immobilization begins with quantitation of the target PCR product by spectrophotometry at 260 nm and subsequent dilution to 40 pg/μL (approximately $10^7$ copies/μL). Eighty picograms of PCR product ($2.0\times10^7$ copies) in 20 μl are immobilized in streptavidin-coated microplate wells manufactured by Abgene (Surrey, UK) and available through Marsh Bio Products (Rochester, N.Y.). Immobilization is performed by a 30 minute room temperature incubation of the PCR product incubation with 20 μl of binding and washing buffer (10 mM Tris-HCL, pH 7.5 1 mM EDA, 2M NaCl). After immobilization, 10 μl TE buffer was added to induce oxidative free radical production upon UV irradiation.

UV irradiation of the target DNA is first begun by preparation of an artificial skin model. Transpore tape (3M Company, St. Paul, Minn.) is used as a seven $cm^2$ artificial skin substrate (approximately 3 $mg/cm^2$). The grooved surface of the tape is similar to the patterns found on human skin. Tape pieces of the same size are placed over all wells with immobilized DNA to mimic the position of DNA within skin cells. Varying thicknesses of the nanotube formulations are evenly applied to the tape over specific wells, leaving other wells without UV protection. EL series UVP ultraviolet lamps will be purchased for varying lengths of UV irradiation. Available through VWR International (West Chester, Pa.), a UVL-28 lamp emits UVA radiation of 365 nm at a relative intensity of 1150 μW/cm2 at a 3 inch distance, and a UVM-28 lamp emits UVB radiation of 302 nm at a relative intensity of 1300 μW/cm2 at a 3 inch distance. Twin model lamps, each containing two single wavelength tubes, were chosen for increased UV intensity to overcome any shielding effects afforded by the artificial skin substrate. Also purchased will be the model J-221 Blak-Ray UV Intensity Meter for quantitation of this shielding effect. The UV dose will be measured through transpore tape alone, and UV irradiation will be optimized once shielding effects of this tape are known. The UV dose afforded by each of the lamps will also be validated by the UV Intensity Meter to assure the absence of contaminating wavelengths.

1. Attempts at nested amplification of the UV-irradiated DNA template are performed directly within the microplate using nested primers.

2. Detection of the extent of amplification is done by visualizing the resultant PCR products by gel electrophoresis and subsequent staining. Decreased amplification infers the presence of UV-induced DNA lesions that inhibit the polymerase. Band intensity is quantitated by an electrophoretic analysis software package, a number of which are commercially available, such as KODAK ID Image Analysis and Nonlinear Dynamics Phoretix 1D Advanced programs. Relative intensities are then calculated using the amplification of an undamaged control and the equation established by Kalinowski and colleagues, as shown in FIG. 5.

Other embodiments and uses of the invention will be apparent to those skilled in the art from consideratio of the specification and practice of the invention disclosed herein. All references cited herein, including all patents and publications for what ever reason, are specifically and entirely incorporated by reference. The specification and examples should be considered exemplary only with the true scope and spirit of the invention embodied within the following claims.

The invention claimed is:

1. A sunscreen composition containing carbon nanotubes.

2. The composition of claim 1, wherein the carbon nanotubes are fullerene structures comprising graphene cylinders closed at either end by caps containing pentagonal rings.

3. The composition of claim 1, wherein the carbon nanotubes divide space into two volumes, an inside volume and an outside volume, wherein the inside and outside volumes are separated by a one-atom thick, impermeable membrane.

4. The composition of claim 1, wherein the carbon nanotubes comprise single graphite layers wrapped into tubes.

5. The composition of claim 1, wherein the carbon nanotubes comprise single-walled carbon nanotubes.

6. The composition of claim 5, wherein the single-walled carbon nanotubes are composed of a single wall of a hexagonally bonded graphene sheet.

7. The composition of claim 1, wherein the carbon nanotubes comprise multi-walled carbon nanotubes.

8. The composition of claim 1, wherein the composition is effective at blocking UV radiation at wavelengths in the range of from 290 to 400 nm.

9. The composition of claim 1, wherein the composition blocks UVA and UVB rays by absorption.

10. The composition of claim 1, wherein the carbon nanotubes are present in said composition at 2% or less by weight of the composition.

11. The composition of claim 1, wherein the carbon nanotubes are not toxic when applied at an effective amount topically as part of a cosmetic composition.

12. The composition of claim 1, wherein the carbon nanotubes completely block UVA and UVB rays.

13. A sunscreen composition containing carbon nanotubes that absorb UV radiation wherein the average length of the carbon nanotubes is one-half of the wavelength of the UV rays that are absorbed by the carbon nanotubes.

14. The composition of claim 13, wherein the average length of the carbon nanotubes is between 145 nm and 200 nm.

15. A composition containing carbon nanotubes, wherein the carbon nanotubes provide protection when applied to the skin from harmful affects of exposure to UVA and UVB radiation.

16. The composition of claim 15, wherein the composition provides an SPF protection of infinity.

17. The composition of claim 15, wherein the composition has no overt biological activity.

18. The composition of claim 15, wherein the carbon nanotubes are in a water-soluble suspension.

19. The composition of claim 18, wherein the carbon nanotubes remain in the water-soluble suspension for an extended period of time.

20. The composition of claim 15, wherein the extended period of time is greater than six months.

21. The composition of claim 15, wherein the carbon nanotubes are derivatized.

22. The composition of claim 15, wherein the composition causes no adverse allergic reactions at an effective amount.

23. The composition of claim 15, wherein the composition contains a sunscreen vehicle.

24. The composition of claim 23, wherein the sunscreen vehicle does not cross-sensitize.

25. The composition of claim 15, which does not produce an autoimmune response at an effective amount.

26. The composition of claim 15, wherein the carbon nanotubes do not break down after a dose of irradiation that is equivalent to moderate sun exposure.

27. The composition of claim 15, wherein the composition does not produce breakdown products that have adverse physical or biological properties.

28. The composition of claim 15, wherein the composition does not penetrate skin after topical application.

29. The composition of claim 15, wherein the composition is biologically insert and stable to UV radiation.

* * * * *